(12) United States Patent
McMahon

(10) Patent No.: US 11,027,056 B2
(45) Date of Patent: Jun. 8, 2021

(54) COMPACT KIT FOR INJECTING LIQUID MEDICATION

(71) Applicant: Douglas F. McMahon, Minneapolis, MN (US)

(72) Inventor: Douglas F. McMahon, Minneapolis, MN (US)

(73) Assignee: Allergy Medical, LLC, Woodbury, MN (US)

( * ) Notice: Subject to any disclaimer, the term of this patent is extended or adjusted under 35 U.S.C. 154(b) by 210 days.

(21) Appl. No.: 16/264,966

(22) Filed: Feb. 1, 2019

(65) Prior Publication Data

US 2019/0231970 A1     Aug. 1, 2019

Related U.S. Application Data

(60) Provisional application No. 62/625,015, filed on Feb. 1, 2018.

(51) Int. Cl.
*A61M 5/00*     (2006.01)
*A61M 5/315*     (2006.01)
(Continued)

(52) U.S. Cl.
CPC .......... *A61M 5/002* (2013.01); *A61M 5/3129* (2013.01); *A61M 5/3153* (2013.01);
(Continued)

(58) Field of Classification Search
CPC .............. A61M 5/002; A61M 5/31501; A61M 5/3129; A61M 5/31595; A61M 5/32;
(Continued)

(56) References Cited

U.S. PATENT DOCUMENTS

| 4,153,056 A | 5/1979 | Silver et al. |
| 4,631,057 A * | 12/1986 | Mitchell ............. A61M 5/3243 604/198 |

(Continued)

FOREIGN PATENT DOCUMENTS

| JP | 07-007650 U | 2/1995 |
| KR | 10-1541740 B1 | 8/2015 |
| WO | 2017034618 A1 | 3/2017 |

OTHER PUBLICATIONS

"Epinephrine in the Treatment of Anaphylaxis," American Academy of Allergy, Asthma & Immunology (AAAAI), Jun. 3, 2012, 3 pages.
(Continued)

*Primary Examiner* — Theodore J Stigell
*Assistant Examiner* — Rachel T. Smith
(74) *Attorney, Agent, or Firm* — Merchant & Gould P.C.

(57) ABSTRACT

An example system for administrating a liquid medication includes a syringe assembly including a barrel portion containing liquid medication, a plunger portion sealingly engaged with the barrel portion to form a chamber for expelling the liquid medication from the barrel portion, and a needle. A ring is positioned about the plunger portion of the syringe assembly, wherein the ring limits movement of the plunger portion in an axial direction as the plunger portion is moved in the axial direction to administer a first dose of the liquid medication. The ring is configured to be modified to allow the plunger to move further in the axial direction to administer a second dose of the liquid medication.

1 Claim, 25 Drawing Sheets

(51) Int. Cl.
*A61M 5/31* (2006.01)
*A61M 5/32* (2006.01)

(52) U.S. Cl.
CPC .... *A61M 5/31501* (2013.01); *A61M 5/31595* (2013.01); *A61M 5/32* (2013.01)

(58) Field of Classification Search
CPC ............ A61M 5/3153; A61M 5/31596; A61M 2005/31598; A61M 2005/1787; A61M 5/284; A61M 5/2448; A61M 2005/2451
See application file for complete search history.

(56) References Cited

U.S. PATENT DOCUMENTS

| | | | |
|---|---|---|---|
| 5,135,514 | A | 8/1992 | Kimber |
| 5,358,489 | A | 10/1994 | Wyrick |
| 5,540,664 | A | 7/1996 | Wyrick |
| 5,601,077 | A * | 2/1997 | Imbert .................. A61M 11/00 128/200.14 |
| 5,665,071 | A | 9/1997 | Wyrick |
| 5,695,472 | A | 12/1997 | Wyrick |
| 5,865,314 | A | 2/1999 | Jacober |
| 6,902,534 | B2 | 6/2005 | Crawford et al. |
| 7,297,136 | B2 | 11/2007 | Wyrick |
| 7,686,016 | B2 | 3/2010 | Wharton et al. |
| 8,057,427 | B2 | 11/2011 | Griffiths et al. |
| 8,945,063 | B2 | 2/2015 | Wotton et al. |
| 2002/0050462 | A1 | 5/2002 | Penney et al. |
| 2002/0074345 | A1 | 6/2002 | Schneider et al. |
| 2002/0143272 | A1 | 10/2002 | Crawford et al. |
| 2003/0132128 | A1 | 7/2003 | Mazur |
| 2006/0129122 | A1 | 6/2006 | Wyrick |
| 2014/0207073 | A1 | 7/2014 | Shang et al. |
| 2015/0157801 | A1 * | 6/2015 | Tran .................. A61M 5/31591 604/208 |
| 2017/0072130 | A1 | 3/2017 | McMahon |

OTHER PUBLICATIONS

"Episnap Epinephrine Convenience Kit," U.S.National Library of Medicine, Jan. 24, 2017, 9 pages.
Wikipedia, "Epinephrine autoinjector," Jan. 30, 2019, 9 pages.
Drugs.com, "Twinject Auto-Injector—FDA prescribing information, side effects and uses," Jun. 1, 2018, 11 pages.
Adamis, "SYMJEPI(TM) (epinephrine) Injection," 2019, 2 pages.
Fikes, Bradley J., "EpiPen rival from San Diego's Adamis nears market," The San Diego Union-Tribune, Nov. 12, 2018, 3 pages.
Sandoz Inc., "SYMJEPI (epinephrine) Injection is the choice that fits," 2019, 8 pages.
International Search Report and Written Opinion of the International Searching Authority for International Patent Application No. PCT/US2015/021001 dated Jun. 24, 2015, 12 pgs.
Sanofi, "How to Use Auvi-Q(TM) (epinephrine injection, USP)," 2013, 1 pg.
International Search Report and Written Opinion in PCT/US2019/016312 dated May 20, 2019, 11 pages.

* cited by examiner

COMPACT KIT FOR INJECTING LIQUID MEDICATION

RELATED APPLICATION(S)

The subject matter of this patent application is related to U.S. patent application Ser. No. 15/126,599 filed on Sep. 16, 2016, the entirety of which is hereby incorporated by reference.

BACKGROUND

Anaphylaxis is a life-threatening allergic reaction. The symptoms of such allergic reactions include severe swelling, breathing problems, or loss of blood pressure. The allergic reactions can be caused by stinging and biting insects, allergy injections, food, medicines, exercise, or unknown causes.

The anaphylaxis is rapid in onset and may cause death. Thus, emergency treatment is necessary before going to doctor or emergency room for more medical treatment. The primary emergency treatment is an injection of epinephrine.

Several types of epinephrine injection devices are used for emergency administration of epinephrine. An example of such injection devices is an epinephrine auto-injector. Typically, a user, either a patient or a spectator, puts a tip of the injector against the middle of the outer side of the patient's upper leg, presses down hard until the needle enters the upper leg through the skin, and holds it in place for a predetermined amount of time. Then, the injector is removed from the upper leg. The remainder of the epinephrine needs to be carefully discarded.

SUMMARY

In one aspect, an example system for administrating a liquid medication includes a syringe assembly including a barrel portion containing liquid medication, a plunger portion sealingly engaged with the barrel portion to form a chamber for expelling the liquid medication from the barrel portion, and a needle. A ring is positioned about the plunger portion of the syringe assembly, wherein the ring limits movement of the plunger portion in an axial direction as the plunger portion is moved in the axial direction to administer a first dose of the liquid medication. The ring is configured to be modified to allow the plunger to move further in the axial direction to administer a second dose of the liquid medication.

DETAILED DESCRIPTION

Figure 1:
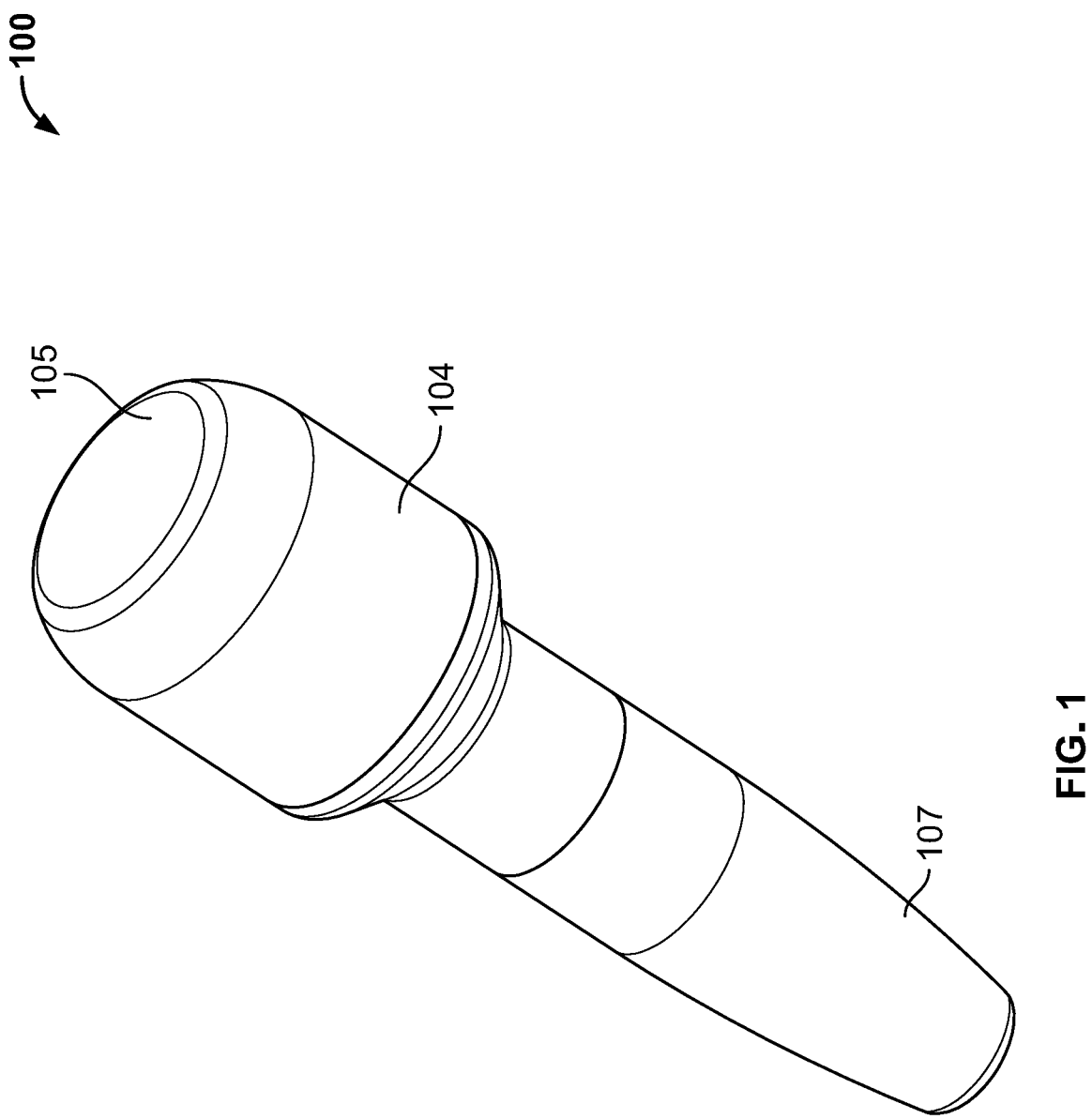
FIG. 1 shows an example kit for injecting liquid medication.
Figure 2:
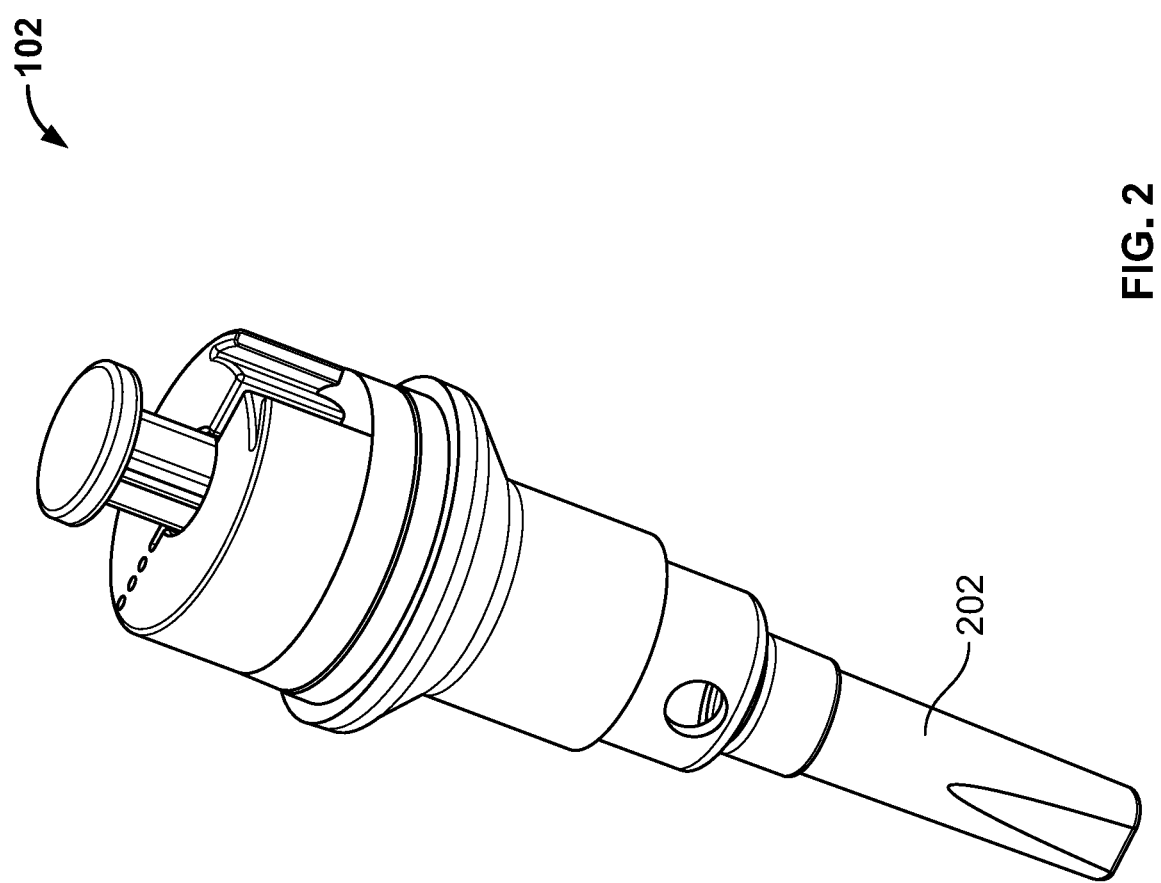
FIG. 2 shows an example injector assembly of the kit of FIG. 1.

Various embodiments will be described in detail with reference to the drawings, wherein like reference numerals represent like parts and assemblies throughout the several views. Reference to various embodiments does not limit the scope of this disclosure. Additionally, any examples set forth in this specification are not intended to be limiting and merely set forth some of many possible embodiments.

FIGS. 1-7 show an example kit 100 for injecting liquid medication. In some embodiments, the kit 100 is used in an emergency situation where a patient needs to be treated with liquid medication. In at least one embodiment, the kit 100 is configured to inject epinephrine into a patient who suddenly shows a life-threatening allergic reaction. In other embodiments, however, the kit 100 is used to inject other types of liquid medication to a patient as a first aid or emergency treatment.

In some embodiments, the kit 100 includes an injection system 102 and a container 104.

The injection system 102 is configured to inject liquid medication to a patient. In some embodiments, the injection system 102 is operated by a patient or an assistant, who can be a parent, medical practitioner, or bystander. The injection system 102 is configured for convenient possession, carrying, and handling. Further, the injection system 102 is dimensioned to contain at least two doses of liquid medication.

The container 104 is configured to contain the injection system 102 therein so that the injection system 102 is conveniently possessed and carried by a patient or any other people who take care of the patient. In some embodiments, the container 104 is only as much sized to include the injection system 102 and small enough to permit a child to easily carry the kit 100 so that, when the child suddenly suffers from anaphylaxis, anybody around the child can take the kit 100 from the child and administer liquid medication (for example, epinephrine) to the child by operating the injection system 102.

In some embodiments, the kit 100 is coupled to any coupling arrangement closely possessed by a patient, such as a necklace worn by a patient, or to a belt loop of pants worn by the patient, so that the kit 100 is not lost and easily found by a spectator or bystander who witnesses sudden life-threatening symptoms of the patient.

The container 104 can have a variety of shapes. In some embodiments, the container 104 has a generally cylindrical vessel that includes at least two portions 105, 107 that are disengaged (e.g., unthreaded or unsnapped) to expose the injector system 102. In other embodiments, the container 104 has a capsule shape. In yet other embodiments, the container 104 is made as a pouch.

The container 104 can be made from a variety of materials. In some embodiments, the container 104 is made from metal, plastic, or fabric. Further, the container 104 is configured to be fastened in various manners. In some embodiments, the container 104 has an outer surface made from rigid materials for protecting the injection system 102 contained therein. In addition, the container 104 can include an inner surface made from cushion materials for further protection of the injection system 102. In some embodiments, the container 104 can be opened or closed with a hook-and-loop fastener, such as Velcro. In other embodiments, the container 104 is fastened with a screw cap arranged at one end of the container 104.

Figure 17:
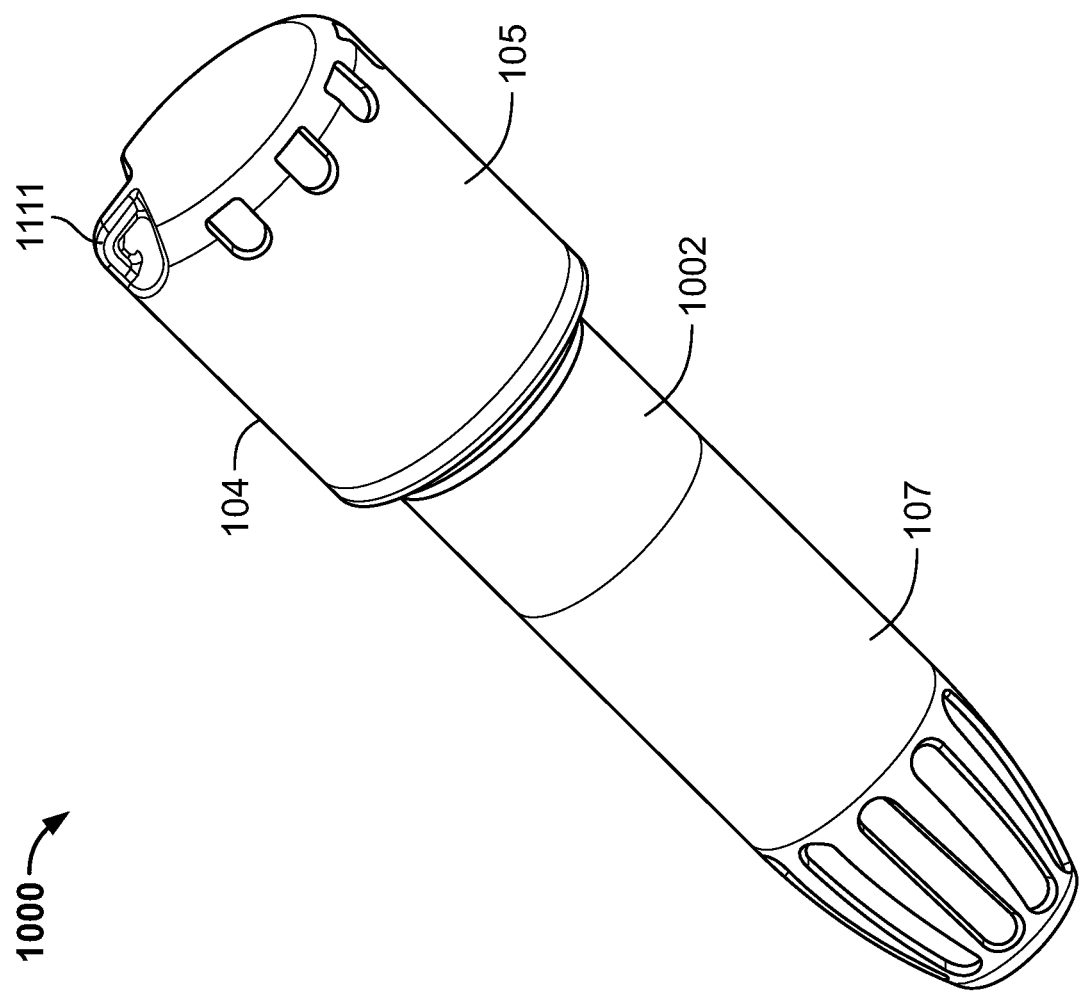
FIG. 17 shows another example kit for injecting liquid medication.

In some embodiments, the container 104 includes a coupling mechanism (see, e.g., coupling mechanism 1111 of FIG. 17) for coupling the container 104 to a coupling arrangement closely possessed by a patient. Examples of the coupling mechanism include a hook or ring configured to be coupled to a keychain, a belt loop, or any other coupling arrangements. For example, the hook or ring is coupled to a necklace worn by a child, or coupled to a belt loop of pants worn by a child. In other examples, the hook or ring is coupled to one or more keys through a keychain.

In some embodiments, the injection system 102 includes a syringe assembly 106 including a barrel portion 112, a plunger portion 114, and a needle shaft 138. See FIG. 7.

In some embodiments, the barrel portion 112 is configured to contain liquid medication therein. In some embodiments, the barrel portion 112 is formed from thermoplastic materials such as polypropylene, polyethylene, polycarbonate and copolymers or any other material suitable for the barrel portion 112.

In some embodiments, the plunger portion 114 includes an elongate plunger body 124 and a gasket 126. The plunger body 124 is sized to fit slidably within the barrel portion 112 by advancing the plunger body 124 into the first end 120 of the barrel portion 112. The gasket 126 is mounted at a head end of the plunger body 124 for occluding the head end of the plunger body 124 and forming a slidable seal with the barrel portion 112 to define a chamber for drawing and expelling liquid medication from the barrel portion 112. In some embodiments, the plunger body 124 is formed from polypropylene, polyethylene, polystyrene, or any other material suitable for the plunger body 124.

The injector system 102 can also include a protective needle cover 202 to at least partially cover the needle shaft 138 to protect the needle shaft 138 before administration of the medication. See FIG. 2.

In some embodiments, the barrel portion 112 of the syringe assembly 106 is configured to contain at least two doses. In one configuration this includes at least 0.3 cc of liquid medication (for example, epinephrine) for each dose (i.e., approximately 0.6 cc total). This is because, for epinephrine injection, many patients only need 0.3 cc or less of epinephrine per dose. An excessive injection of epinephrine can cause dangerously high blood pressure, stroke, or death, and thus, it is very important to limit a dosage of epinephrine, as described herein. However, in some instances, a single does is not effective. In such instances, the second dose can be administered, as described further below.

In other embodiments, the syringe assembly 106 is configured to contain the liquid medication of more than 0.3 cc but not more than 0.5 cc per dose (i.e., 0.6 cc to 1.0 cc total). In yet other embodiments, the syringe assembly 106 is configured to contain the liquid medication of less than 0.3 cc (i.e., less than 0.6 cc total).

Figure 3:
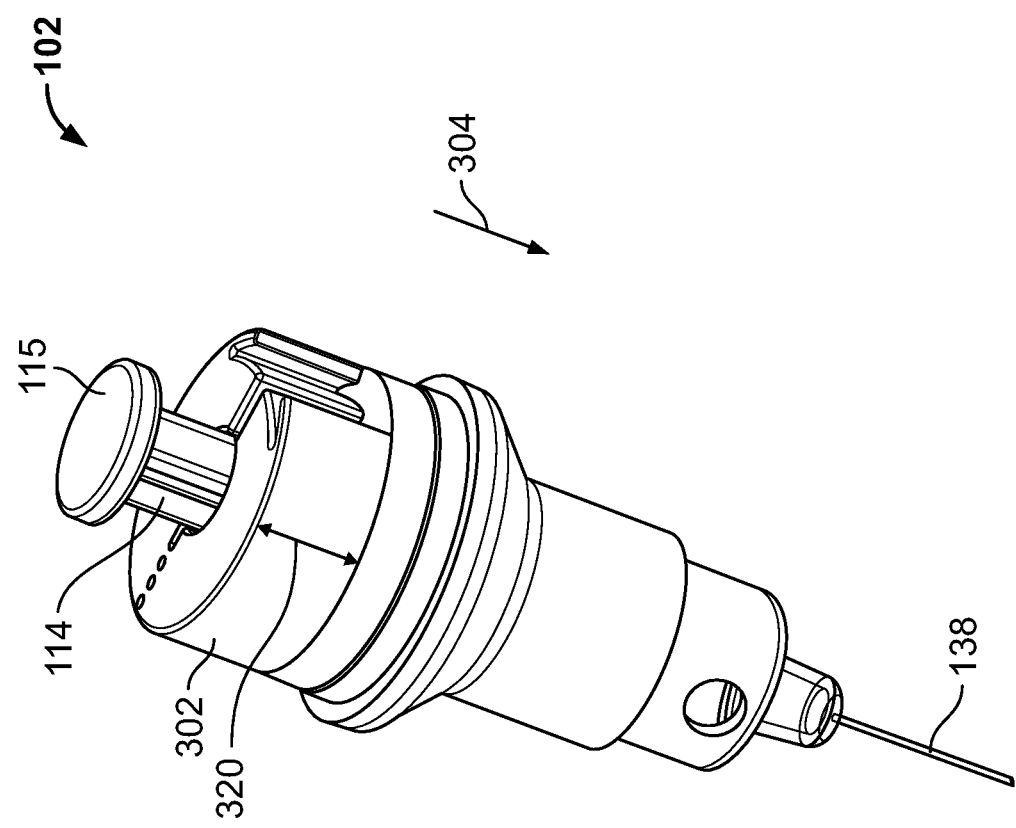
FIG. 3 shows another view of the injector assembly of FIG. 2 ready to administer a first dose of medication.

Referring now to FIG. 3, the container 104 and the protective needle cover 202 are removed to expose the injector system 102. In this configuration, the injector system 102 is configured to administer a first dose of the medication.

Figure 4:
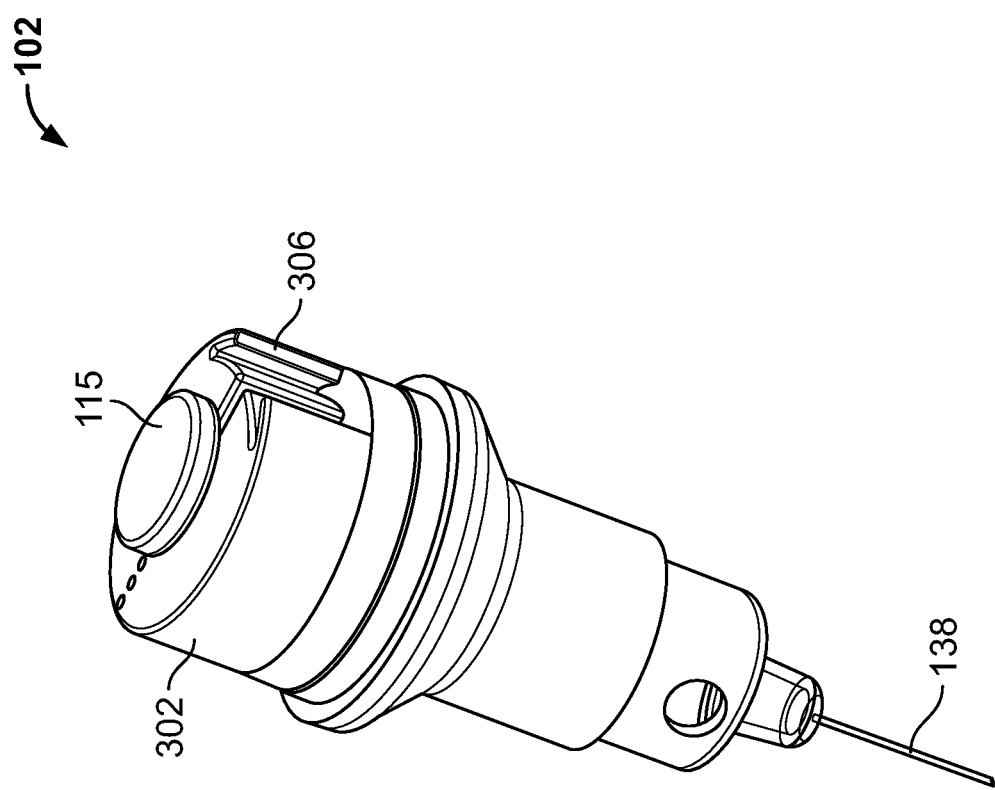
FIG. 4 shows another view of the injector assembly of FIG. 2 after administration of the first dose of medication.

To administer the first dose, the needle shaft 138 is placed into the patient's skin, and the plunger portion 114 is pushed in an axial direction 304 into the barrel portion 112 to force the first dose of the medication through the needle shaft 138 and into the patient. The first dose is complete when a head 115 of the plunger portion 114 bottoms out against a ring 302 positioned about the plunger portion 114. A height 320 of the ring 302 is configured to allow the plunger portion 114 to travel in the axial direction 304 a proper amount for the first dose. At that point, a proper amount of the medication has been forced out of the barrel portion 112 for the first dose, as shown in FIG. 4.

Figure 5:
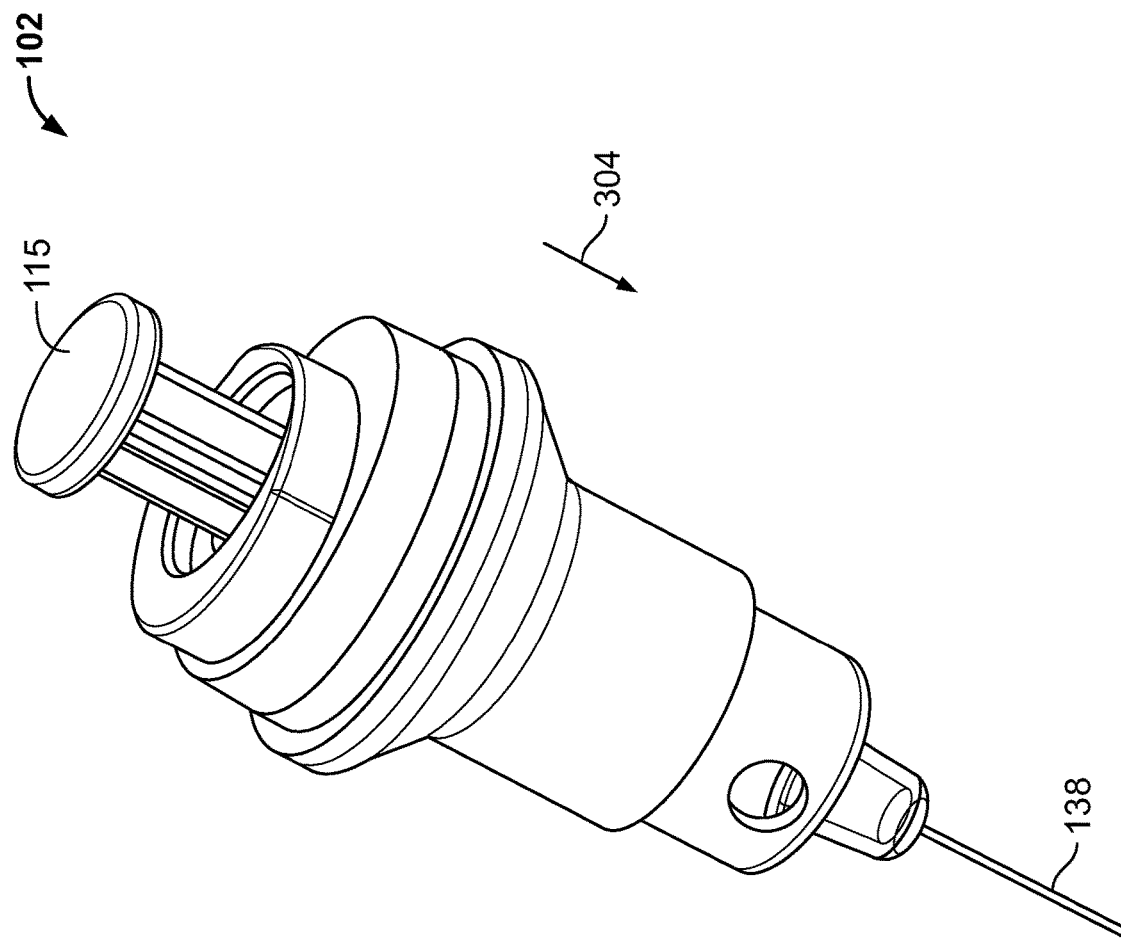
FIG. 5 shows another view of the injector assembly of FIG. 2 ready to administer a second dose of medication.
Figure 6:
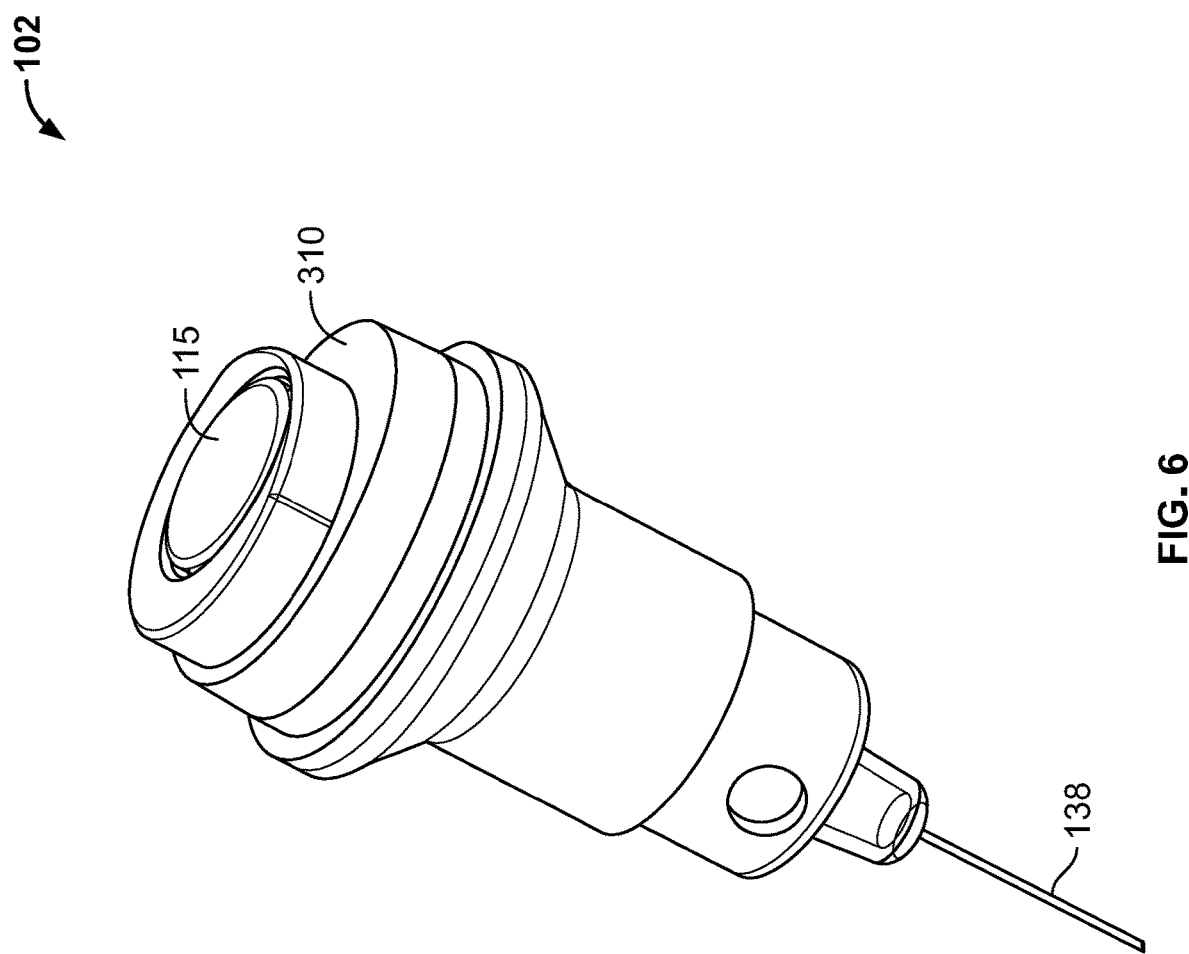
FIG. 6 shows another view of the injector assembly of FIG. 2 after administration of the second dose of medication.
Figure 7:
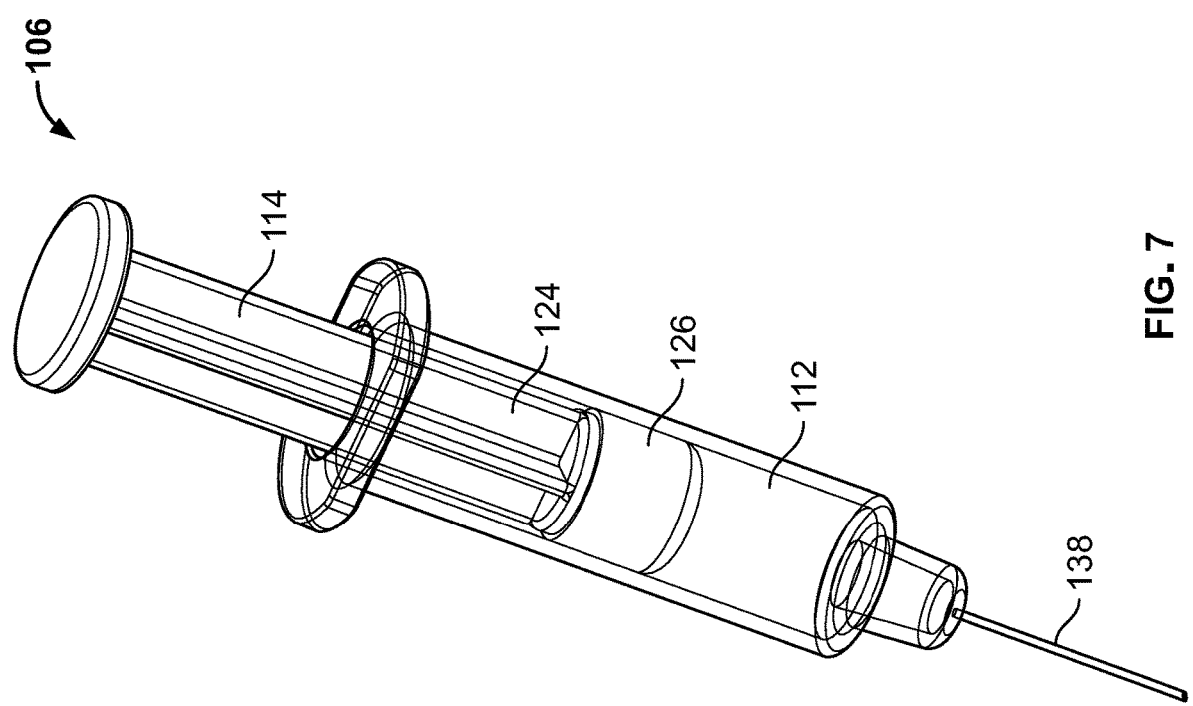
FIG. 7 shows an example syringe assembly of the injector assembly of FIG. 2.
Figure 8:
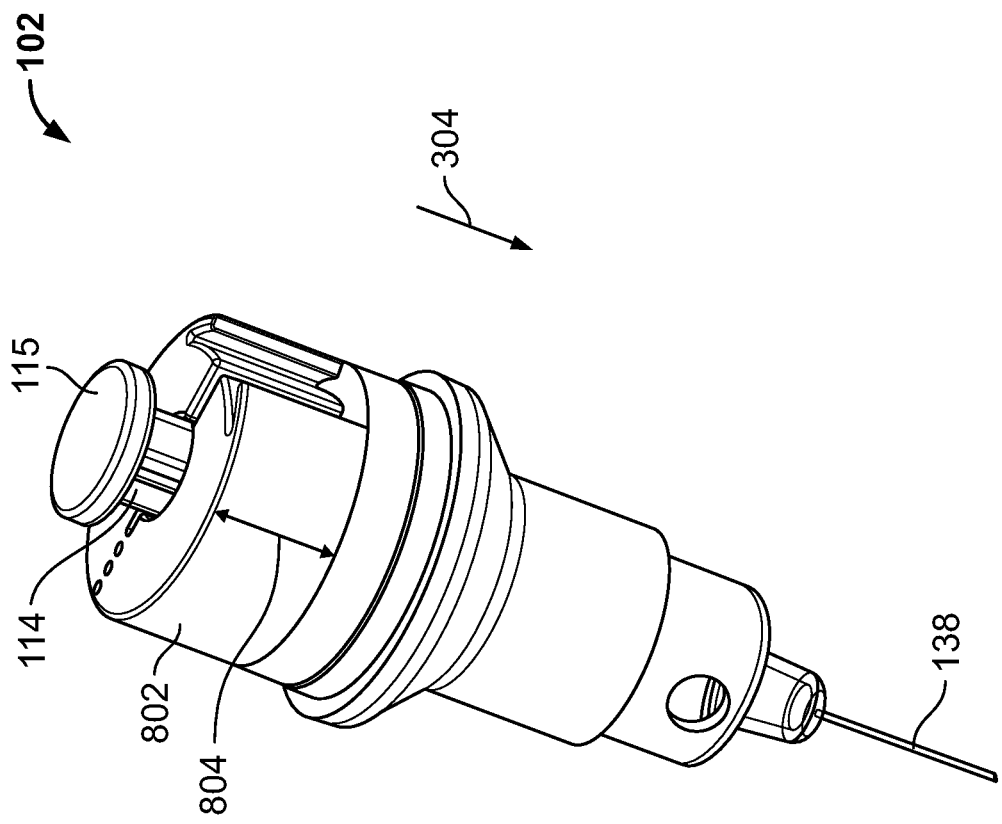
FIG. 8 shows another view of the injector assembly of FIG. 2 ready to administer a first dose of medication.
Figure 9:
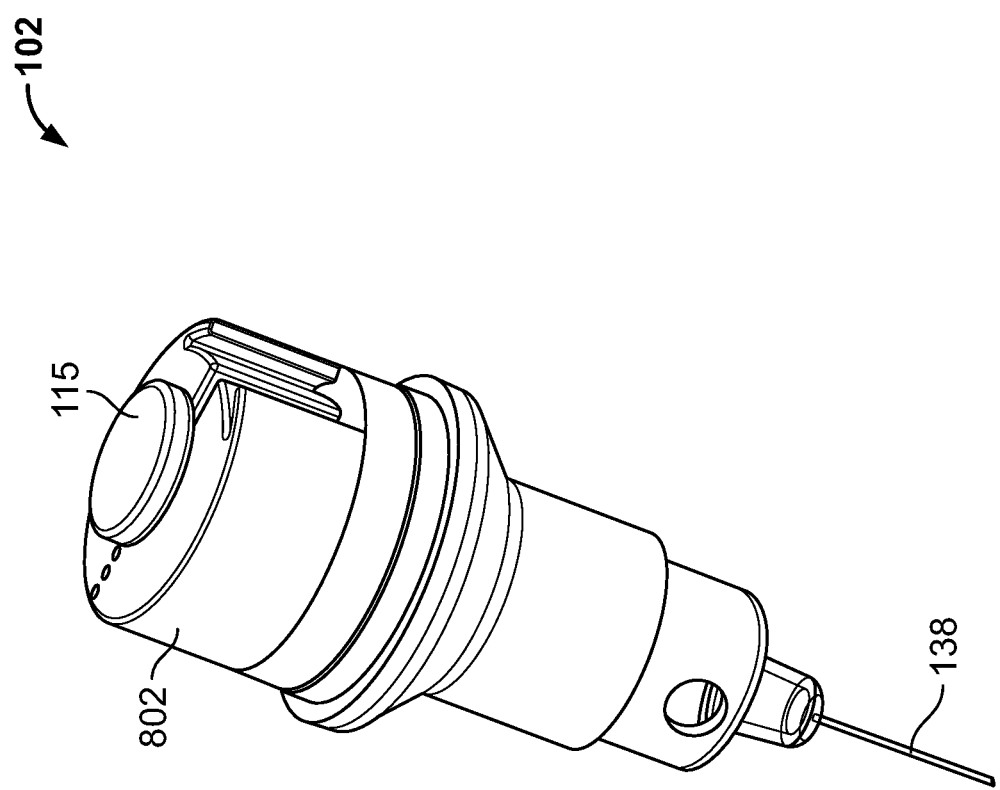
FIG. 9 shows another view of the injector assembly of FIG. 8 after administration of the first dose of medication.

If a second dose needs to be administered, the ring 302 can be removed from the injector system 102. This is accomplished by pulling on a side 306 of the ring 302 to pull the ring apart and remove it from about the plunger portion 114. This is depicted in FIG. 5. Once removed, the plunger portion 114 can be pushed further in the axial direction 304 into the barrel portion 112 to force the second dose of the medication through the needle shaft 138 and into the patient. The second dose is complete when the head 115 of the plunger portion 114 bottoms out against a body 310 of the injector system 102. At that point, a proper amount of the medication has been forced out of the barrel portion 112 for the second dose, as shown in FIG. 6.

Referring now to FIGS. 8-11, an alternate design for the injector system 102 is shown. The majority of the components of the injector system 102 are the same as those described above, except a different ring 802 is provided having a greater height 804. This modifies the travel of the plunger portion 114 in the axial direction 304 to limit the amount of medication to be administered in the first dose. Specifically, since the height 804 is greater, the plunger portion 114 moves less in the axial direction 304 before the head 115 contacts the ring 802 (see FIG. 9), thereby providing less medication. Such a configuration could be used to administer a dose to a child or smaller adult who needs less medication.

Figure 10:
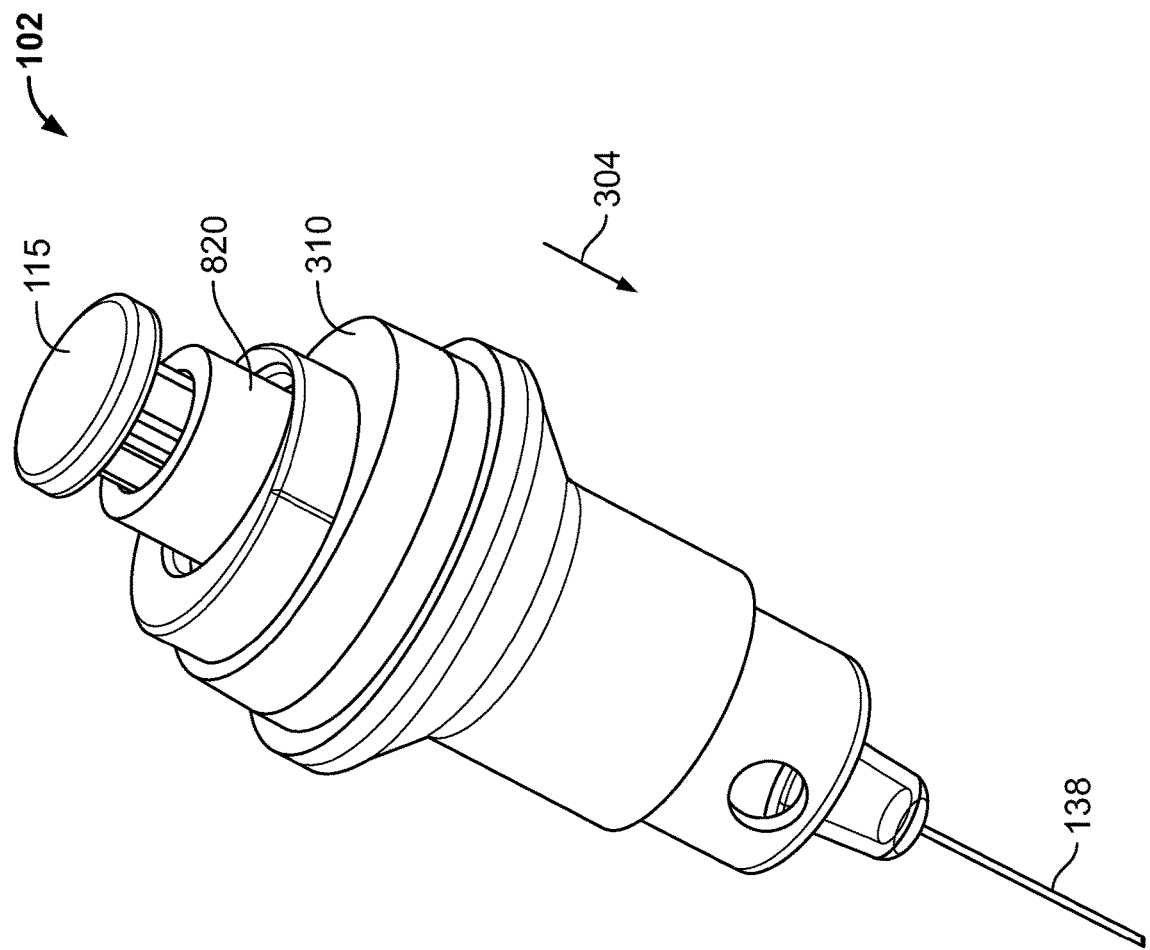
FIG. 10 shows another view of the injector assembly of FIG. 8 ready to administer a second dose of medication.
Figure 11:
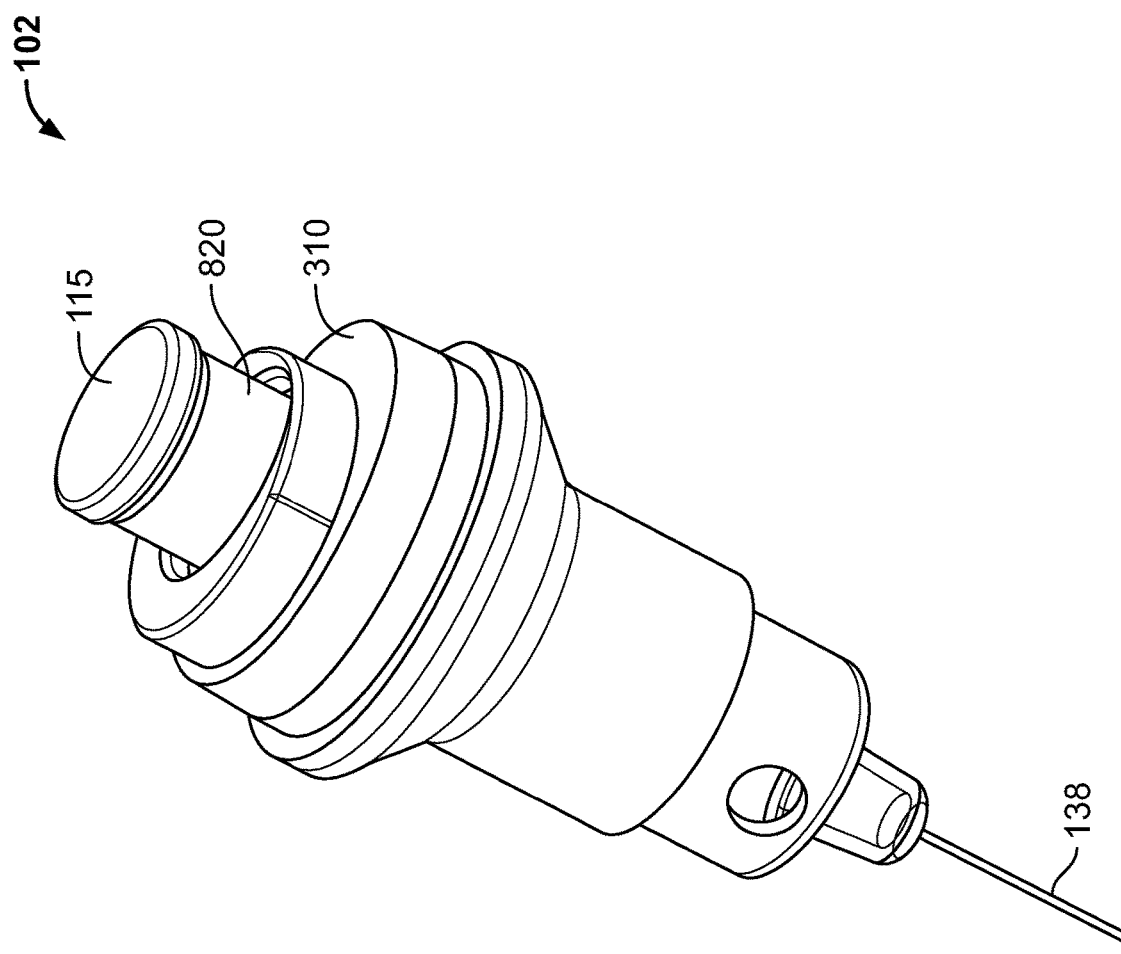
FIG. 11 shows another view of the injector assembly of FIG. 8 after administration of the second dose of medication.
Figure 12:
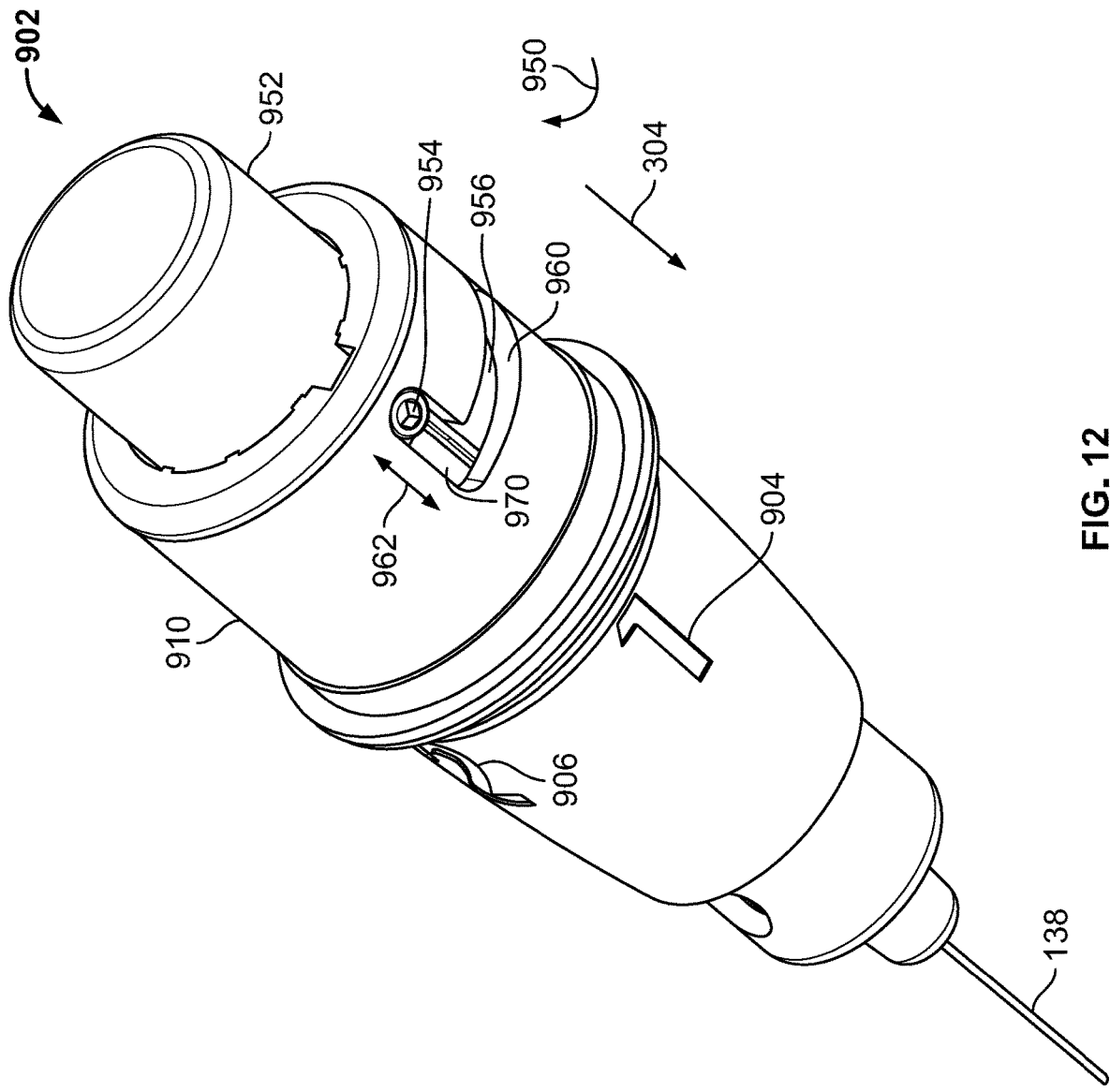
FIG. 12 shows another example injector assembly ready to administer a first dose of medication.

As shown in FIG. 10, the ring 802 can be removed after the first dose to allow the second dose to be administered, if needed. A ring 820 on the body 310 limits the travel of the plunger portion 114 so that when the head 115 contacts the ring 820, a proper amount of medication has been administered for the second dose of medication. See FIG. 11.

As illustrated, the configuration of the rings (e.g., the relative heights) can dictate the amount of medication that is administered for each dose. In such examples, the amount of medication that is provided in the barrel portion 112 need not be exact. In other words, the amount of medication provided in the barrel portion 112 simply needs to be at least the amount required for the first and second doses combined. Any medication that is left in the barrel portion 112 after administration of the first dose and optional second dose can be discarded with the injector system 102.

In this configuration, the kit 100 can be filled with a given quantity of medication regardless of application. The rings can be applied as needed to dictate the amount of medication that is delivered for the first and second doses for a given application, such as for an adult versus a child.

FIGS. 12-16 show an example of another injection system 902. As many of the concepts and features are similar to the injection system 102 described above, like or similar features or elements are shown, and the same reference numbers will be used where possible. The following description for this example will be limited primarily to the differences from the injection system 102.

Figure 16:
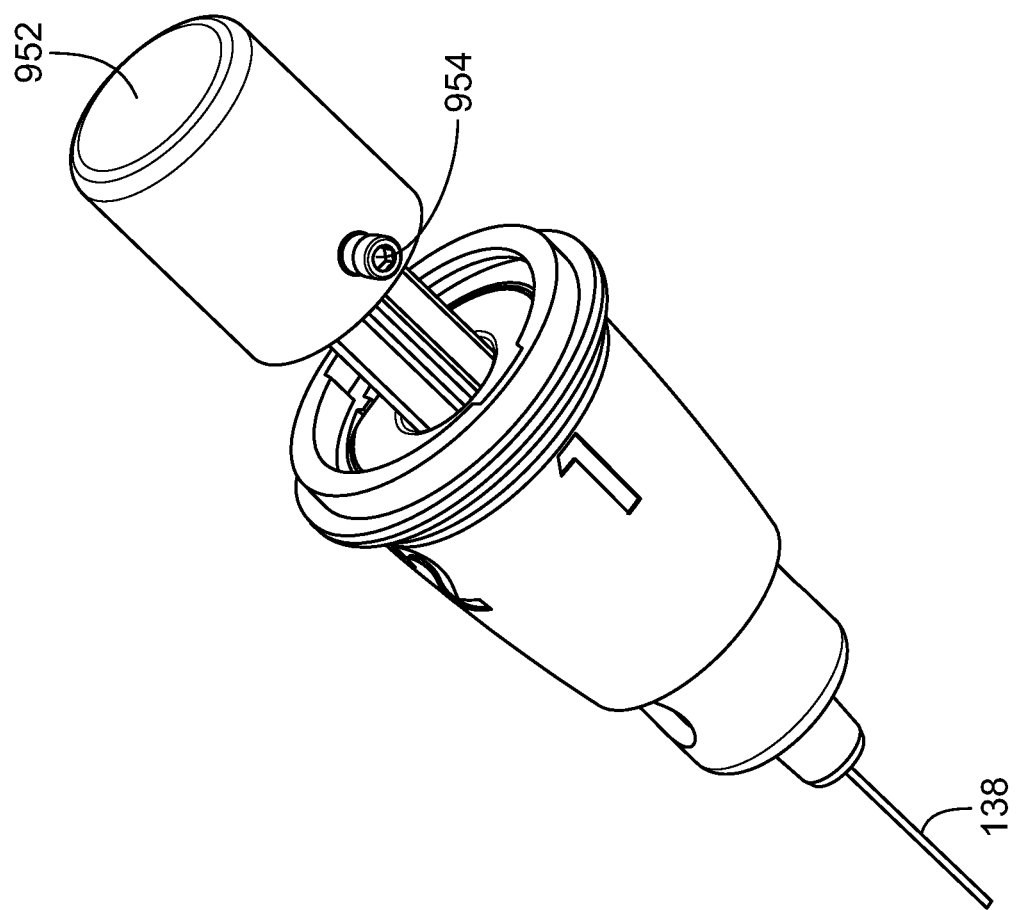
FIG. 16 shows another view of the injector assembly of FIG. 12.

The injection system 902 includes a plunger portion 952 with a projection 954 (see FIG. 16). The injection system 902 further includes a ring 910 positioned about that defines a channel 956 in which the projection 954 rides.

Figure 13:
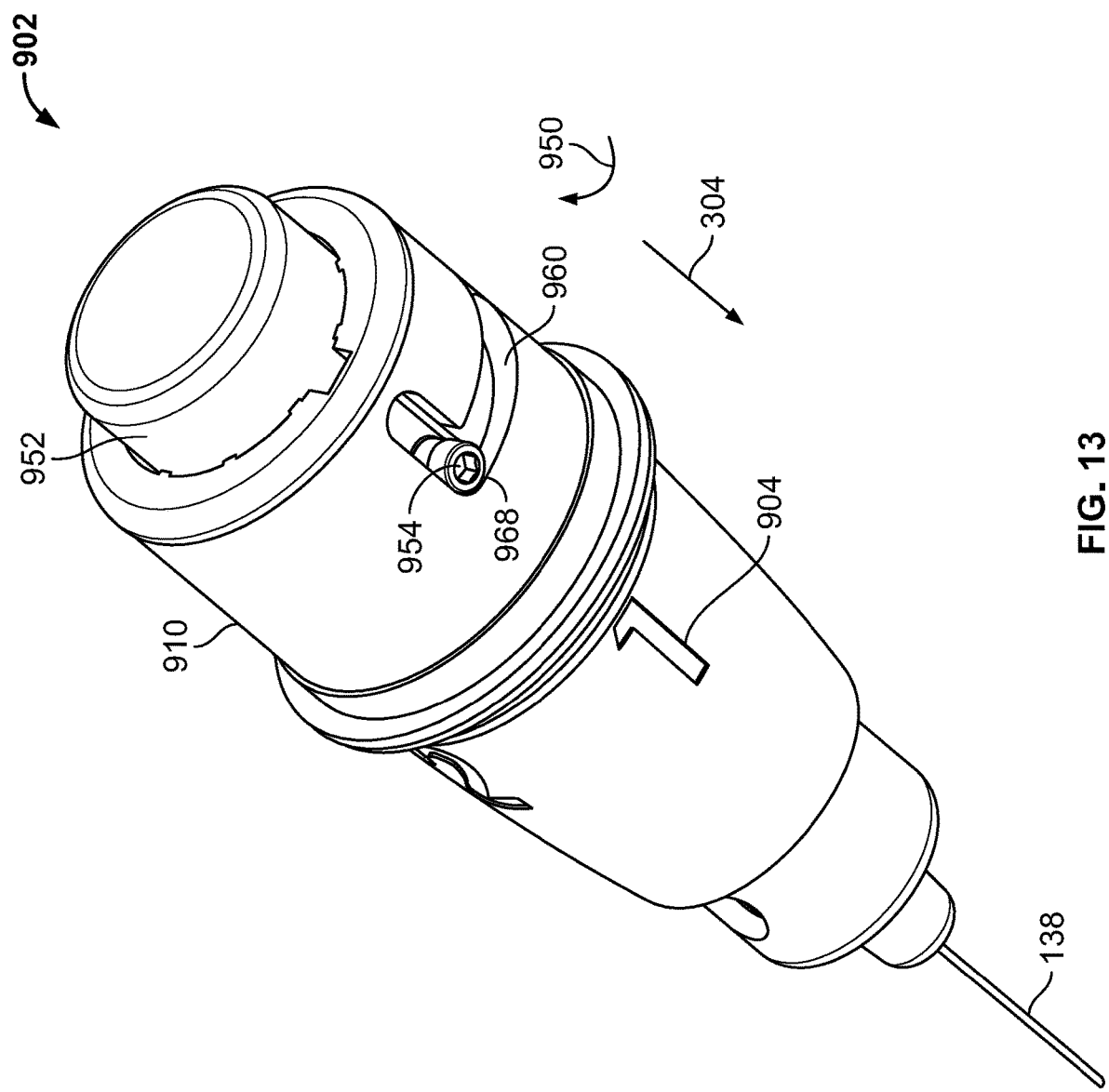
FIG. 13 shows another view of the injector assembly of FIG. 12 after administration of the first dose of medication.

When the ring 910 is in a first rotational position 904 ("1"), the plunger portion 952 can be moved in the axial direction 304 so that the projection 954 rides in a first dose portion 970 of the channel 956 until the projection 954 reaches a first bottom portion 968, as shown in FIG. 13. In this position, the first dose of medication has been administered.

Figure 14:
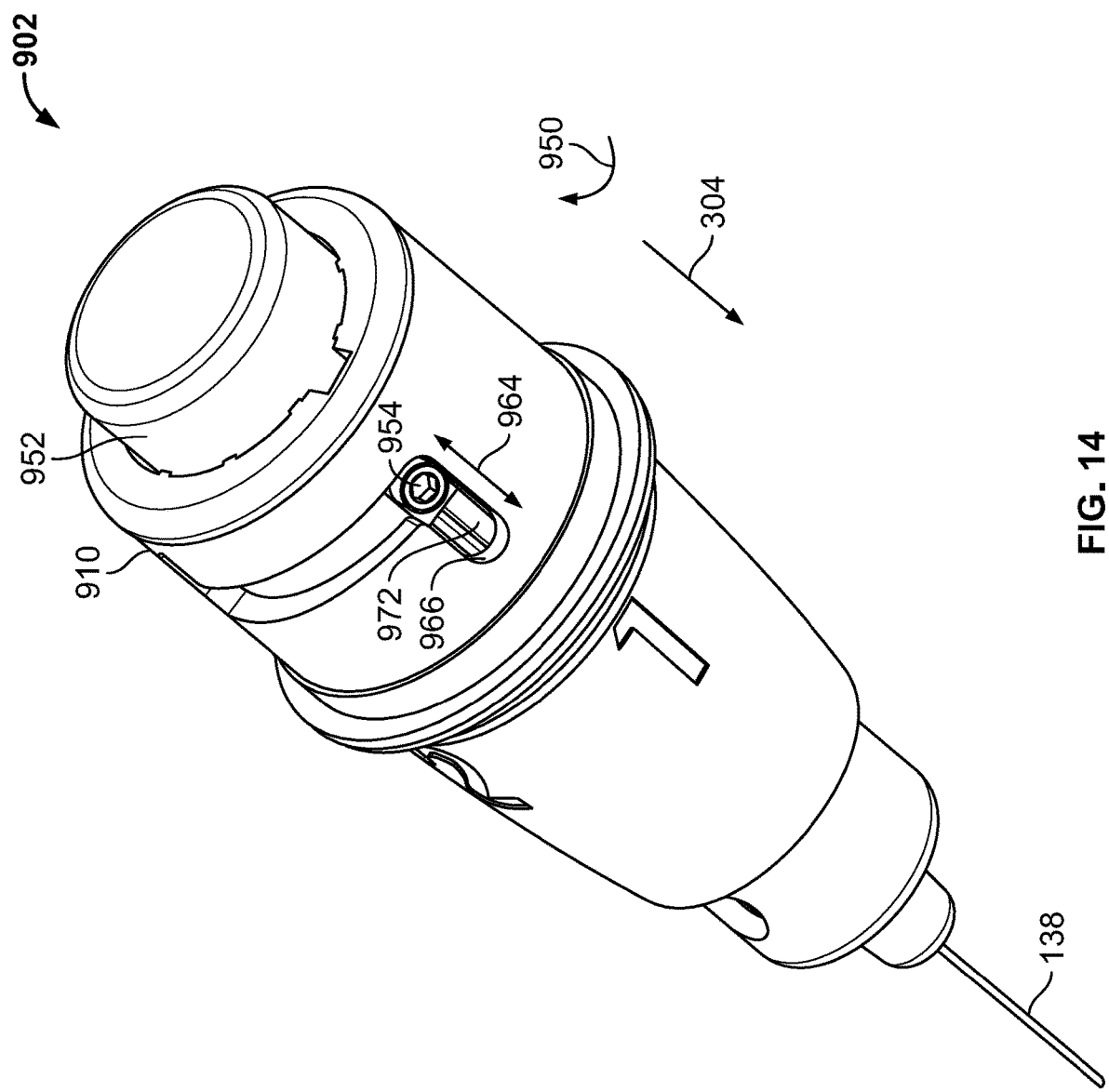
FIG. 14 shows another view of the injector assembly of FIG. 12 ready to administer a second dose of medication.
Figure 15:
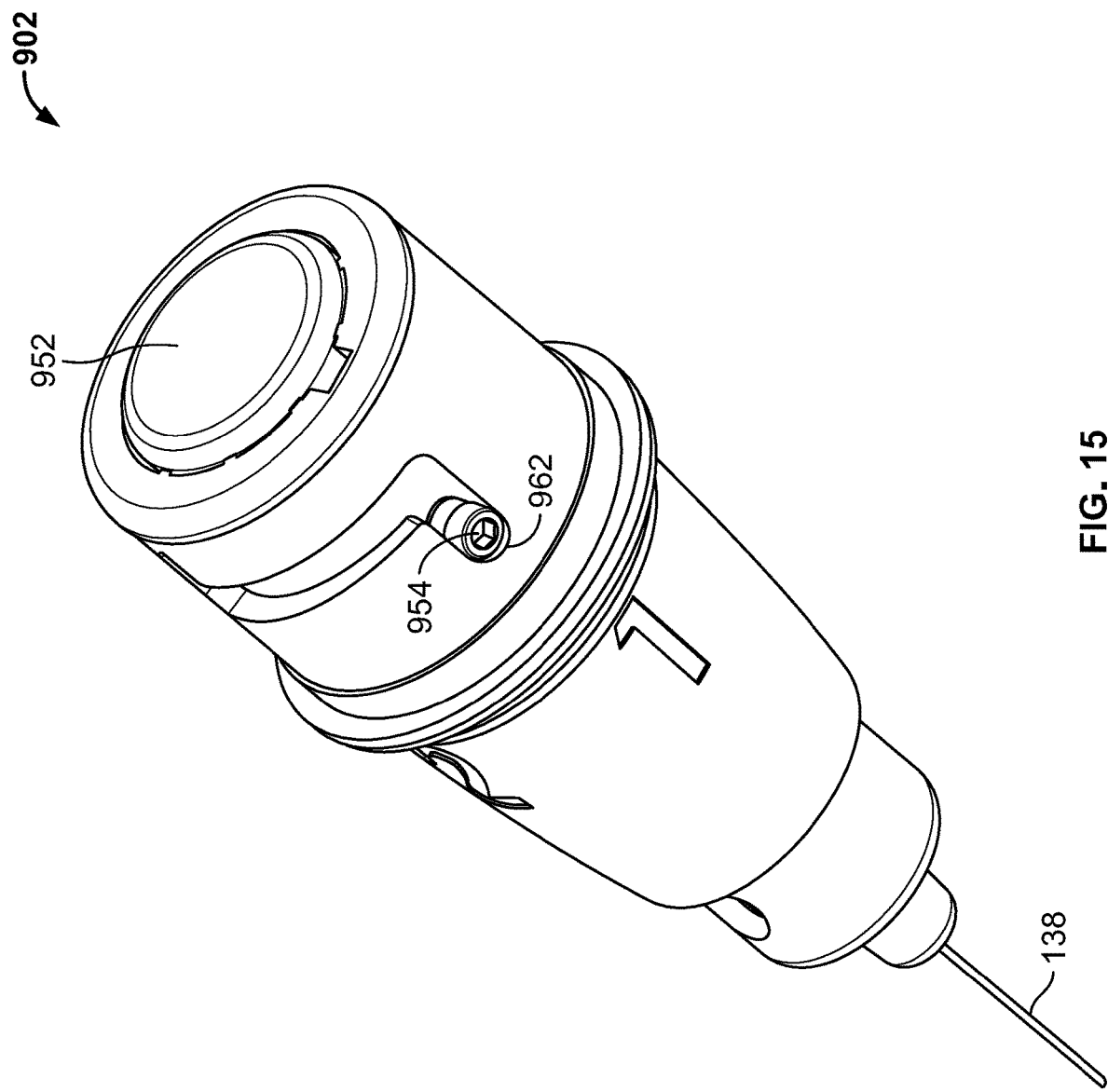
FIG. 15 shows another view of the injector assembly of FIG. 12 after administration of the second dose of medication.

If a second dose is needed, the ring 910 can be twisted in a direction 950 so that the projection 954 rides into the channel 956 along a transition portion 960 to reach a second dose portion 972 of the channel 956, as shown in FIG. 14. This is indicates as the second rotational position 906 ("2"). In this position, the plunger portion 952 can be moved further in the axial direction 304 so that the projection 954 rides in the first dose portion 972 of the channel 956 until the projection 954 reaches a second bottom portion 966, as shown in FIG. 14. In this position, the second dose of medication has been administered.

By modifying lengths 962, 964 (e.g., heights) of the first and second dose portions 970, 972, the travel of the plunger portion 952 can be modified to dictate the amount of medication that is delivered. In other words, the lengths 970, 972 can be shortened to reduce the amount of medication delivered or lengthened to increase the amount of medication delivered. In a similar manner to that described above, the amount of medication provided in the barrel portion 112 can remain constant between devices, and the configuration of the ring 910 modified to modify the amount of medication delivered.

FIGS. 17-23 show an example of another kit 1000 with an injection system 1002. As many of the concepts and features are similar to the injection systems 102, 902 described above, like or similar features or elements are shown, and the same reference numbers will be used where possible. The following description for this example will be limited primarily to the differences from the injection systems 102, 902.

Figure 18:
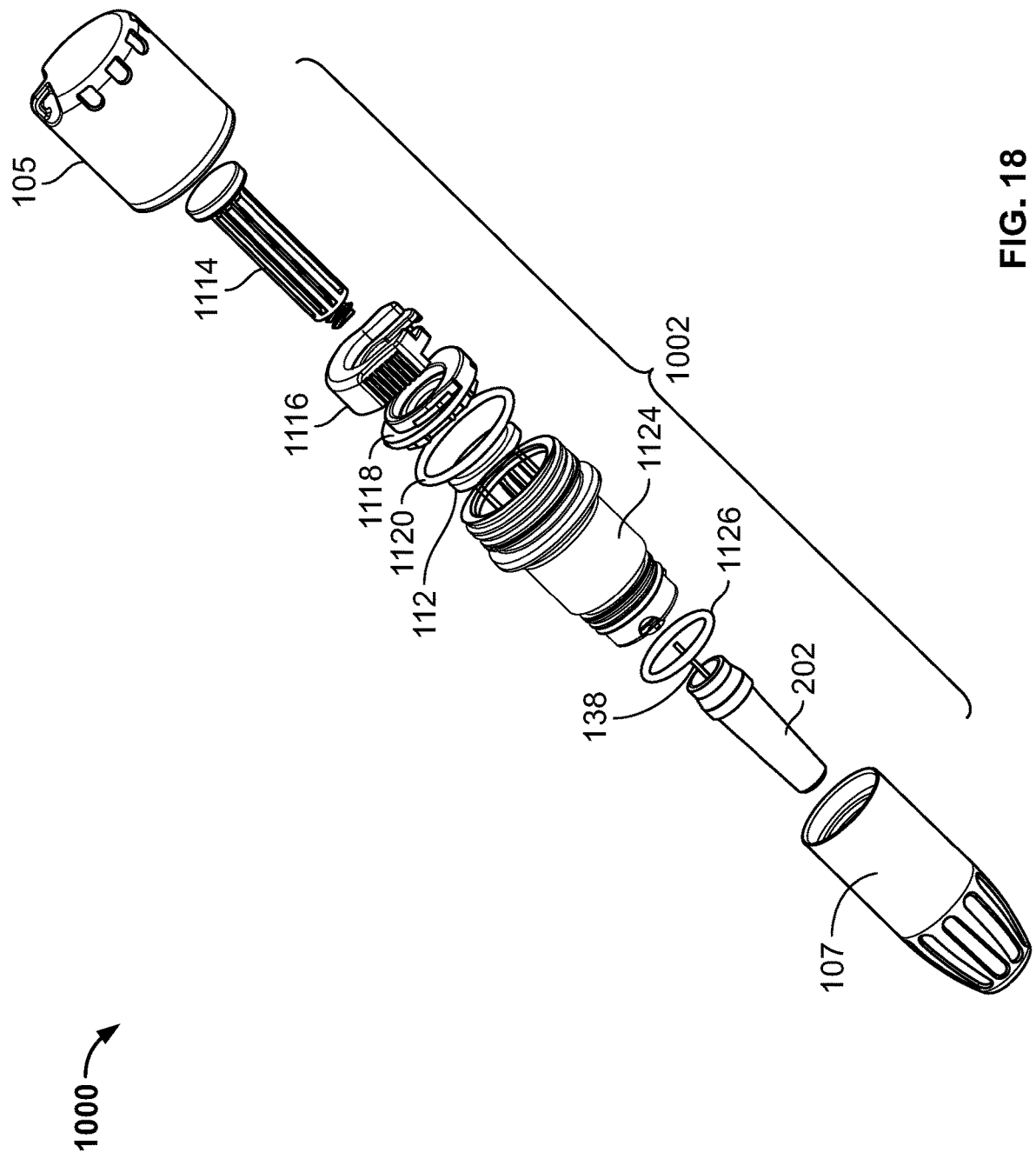
FIG. 18 shows an exploded view of the kit of FIG. 17.

As depicted in FIG. 18, the injection system 1002 includes a main body 1124 threadingly-coupled to portions 105, 107 of the container 104 of the kit 1000. O-rings 1120, 1126 function to seal the container 104 prior to opening.

A plunger portion 1114 moves within the barrel portion 112 to administer multiple doses of medication. A ring 1116 limits movement of the plunger portion 1114 to administer proper doses, as described further below. A cap 1118 seals the main body 1124.

Figure 19:
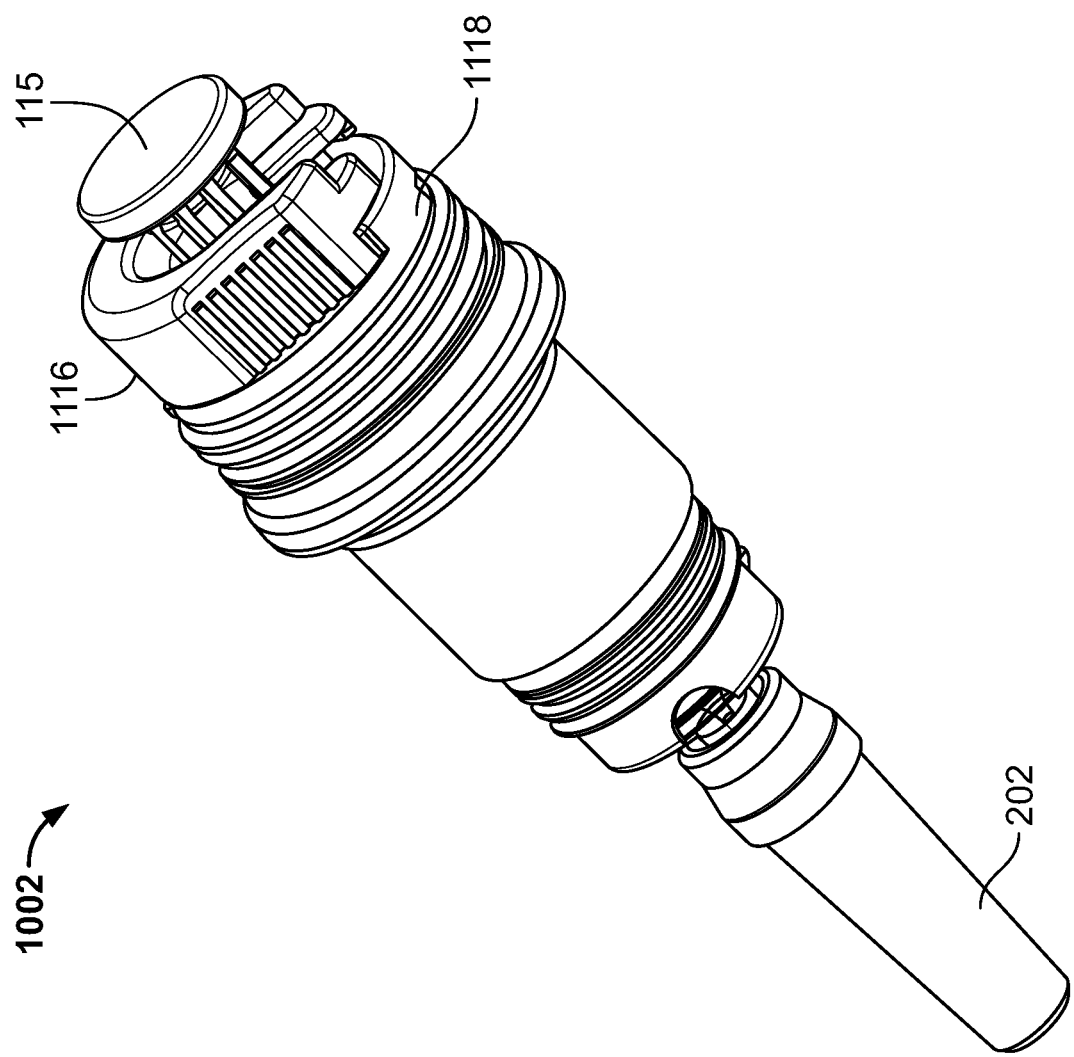
FIG. 19 shows an example injector assembly of the kit of FIG. 17.
Figure 20:
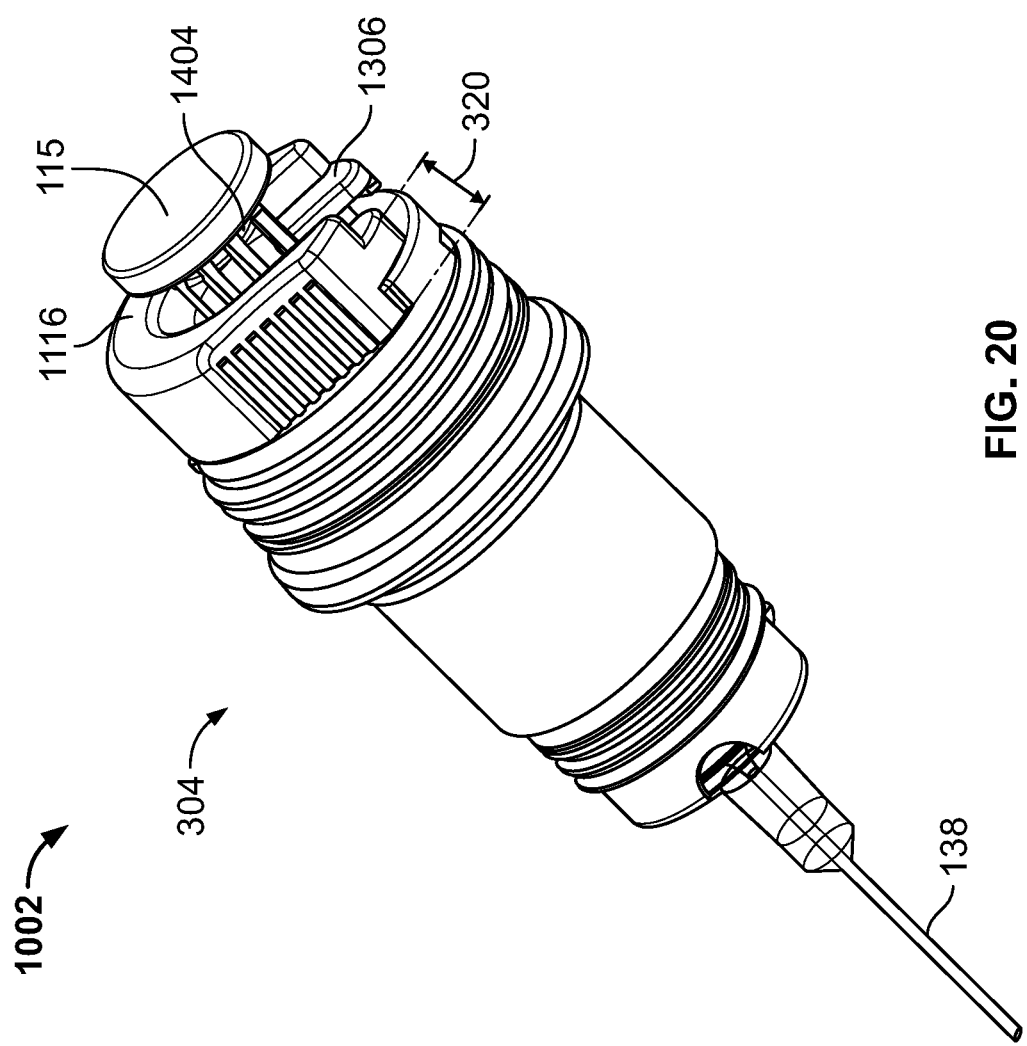
FIG. 20 shows another view of the injector assembly of FIG. 19 ready to administer a first dose of medication.

To administer the first dose, the portions 105, 107 of the container 104 are removed, as shown in FIG. 19. The protective needle cover 202 is removed to expose the needle shaft 138, as shown in FIG. 20.

Figure 21:
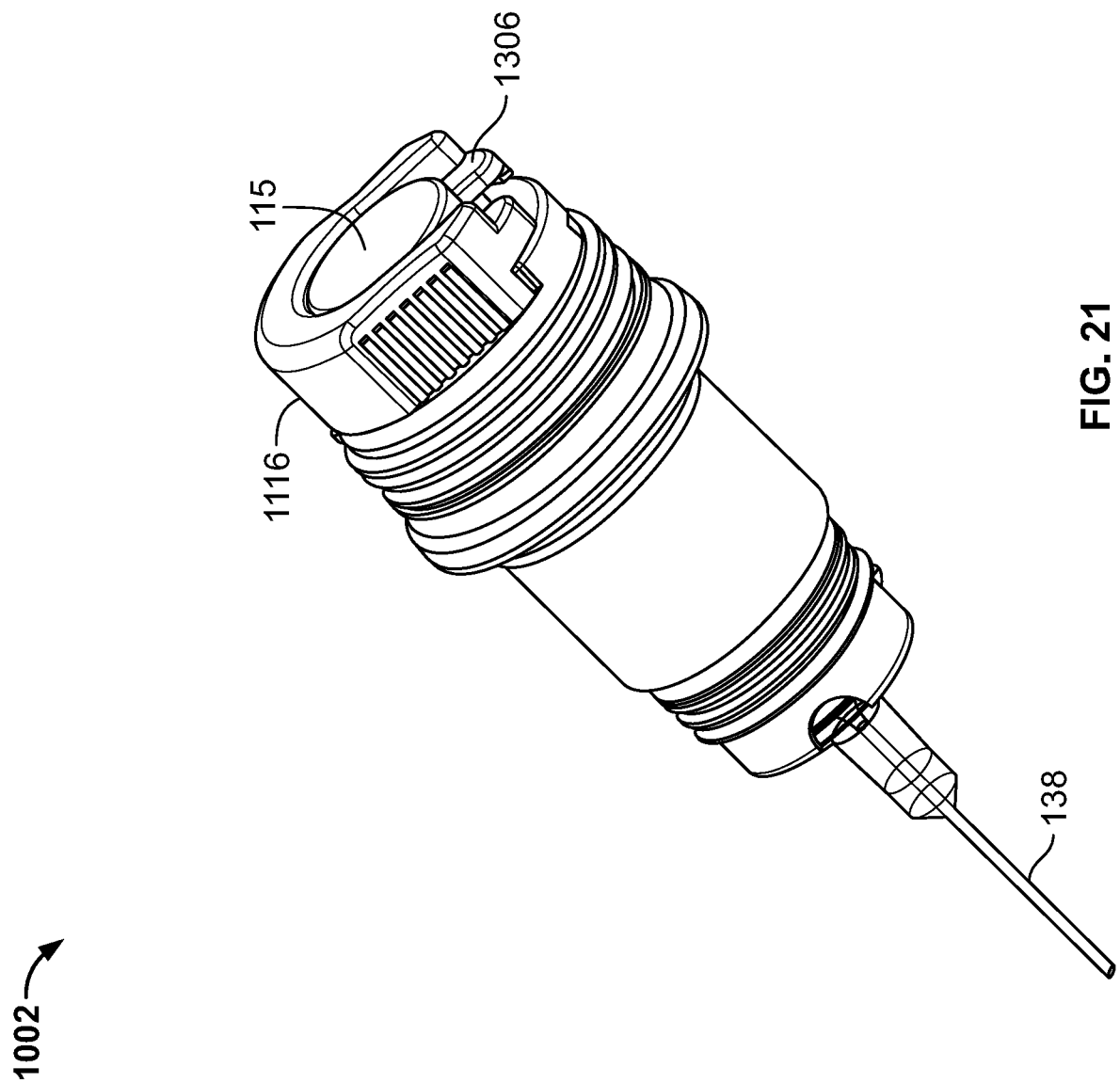
FIG. 21 shows another view of the injector assembly of FIG. 20 after administration of the first dose of medication.

The needle shaft 138 is placed into the patient's skin, and the plunger portion 1114 is pushed in the axial direction 304 into the barrel portion 112 to force the first dose of the medication through the needle shaft 138 and into the patient, as shown in FIG. 21. The first dose is complete when the head 115 of the plunger portion 114 bottoms out against a ledge 1306 formed by the ring 1116 positioned about the plunger portion 1114. The height 320 of the ledge 1306 of the ring 1116 is configured to allow the plunger portion 1114 to travel in the axial direction 304 a proper amount for the first dose. At that point, a proper amount of the medication has been forced out of the barrel portion 112 for the first dose.

Figure 22:
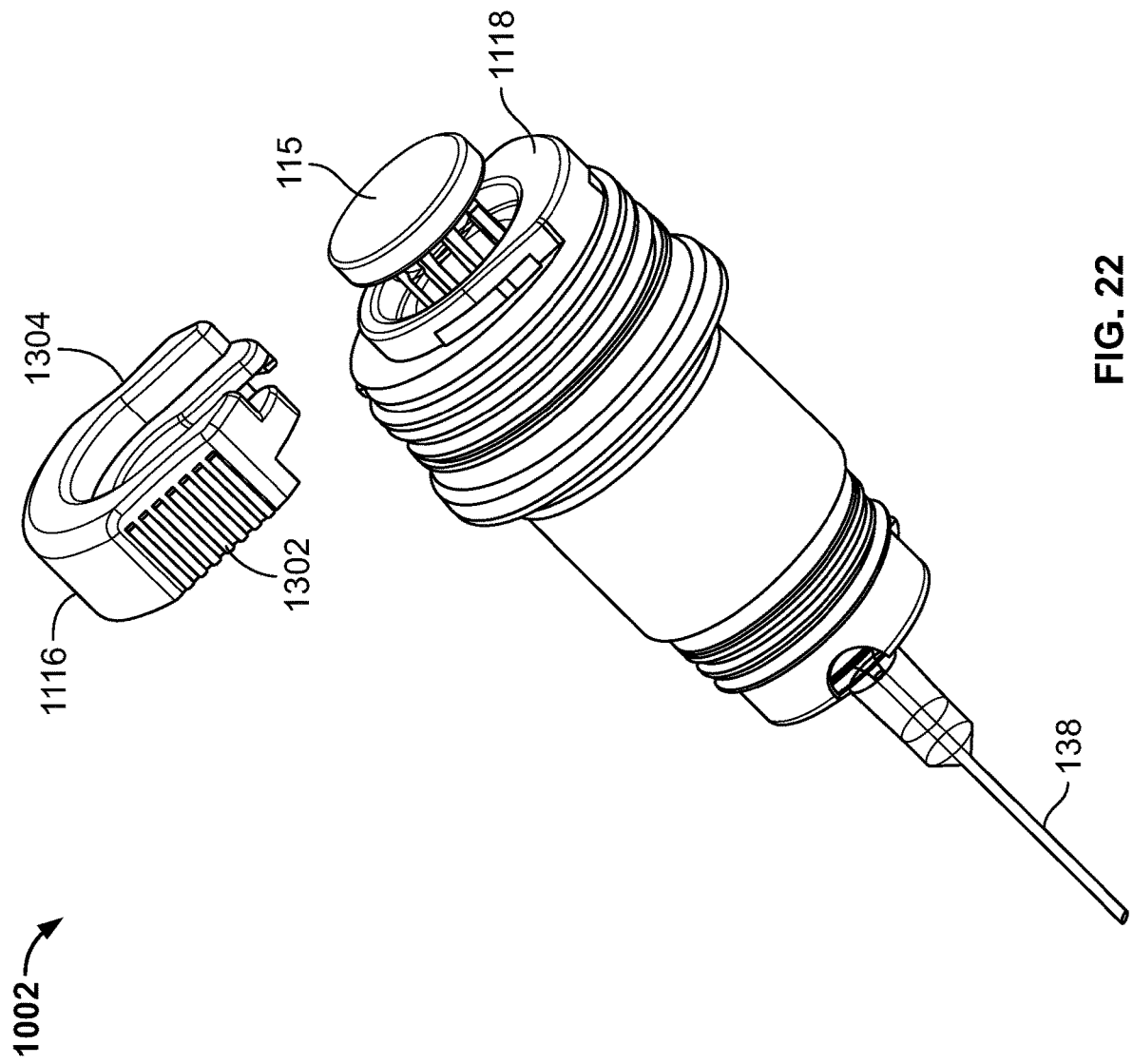
FIG. 22 shows another view of the injector assembly of FIG. 20 ready to administer a second dose of medication.

If a second dose needs to be administered at a later point, the ring 1116 can be removed, as shown in FIG. 22. For example, if a first does of medication is insufficient, a second dose can be administered a few minutes (e.g., 5 minutes) later. This is accomplished by pulling on sides 1302, 1304 of the ring 1116 to remove the ring 1116 from about the plunger portion 1114.

Figure 24:
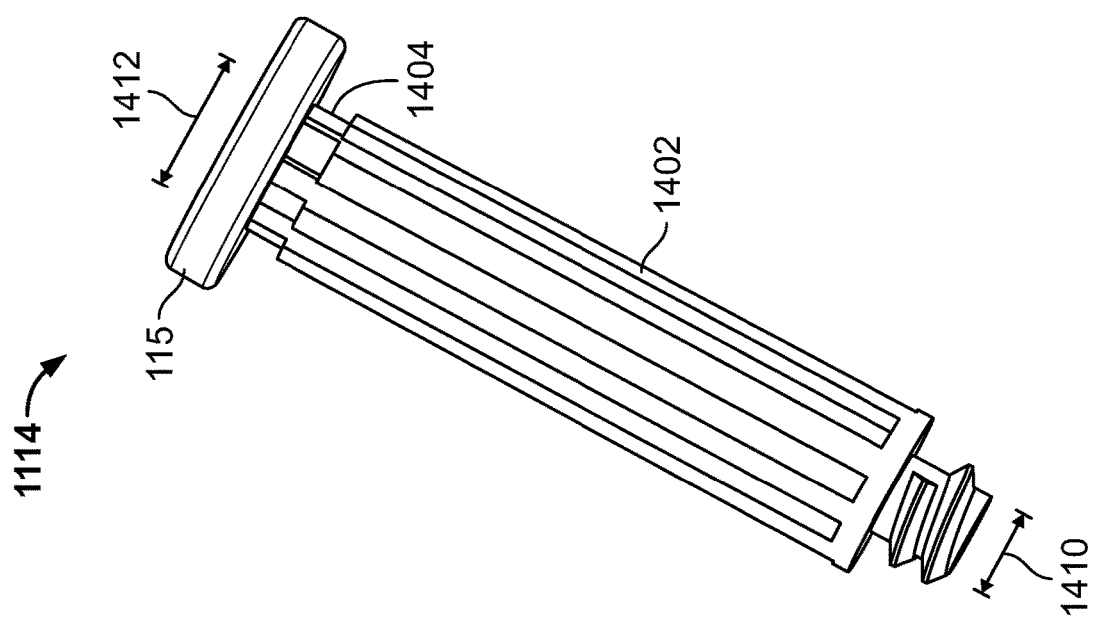
FIG. 24 shows an example plunger portion of the injector assembly of FIG. 20.
Figure 25:
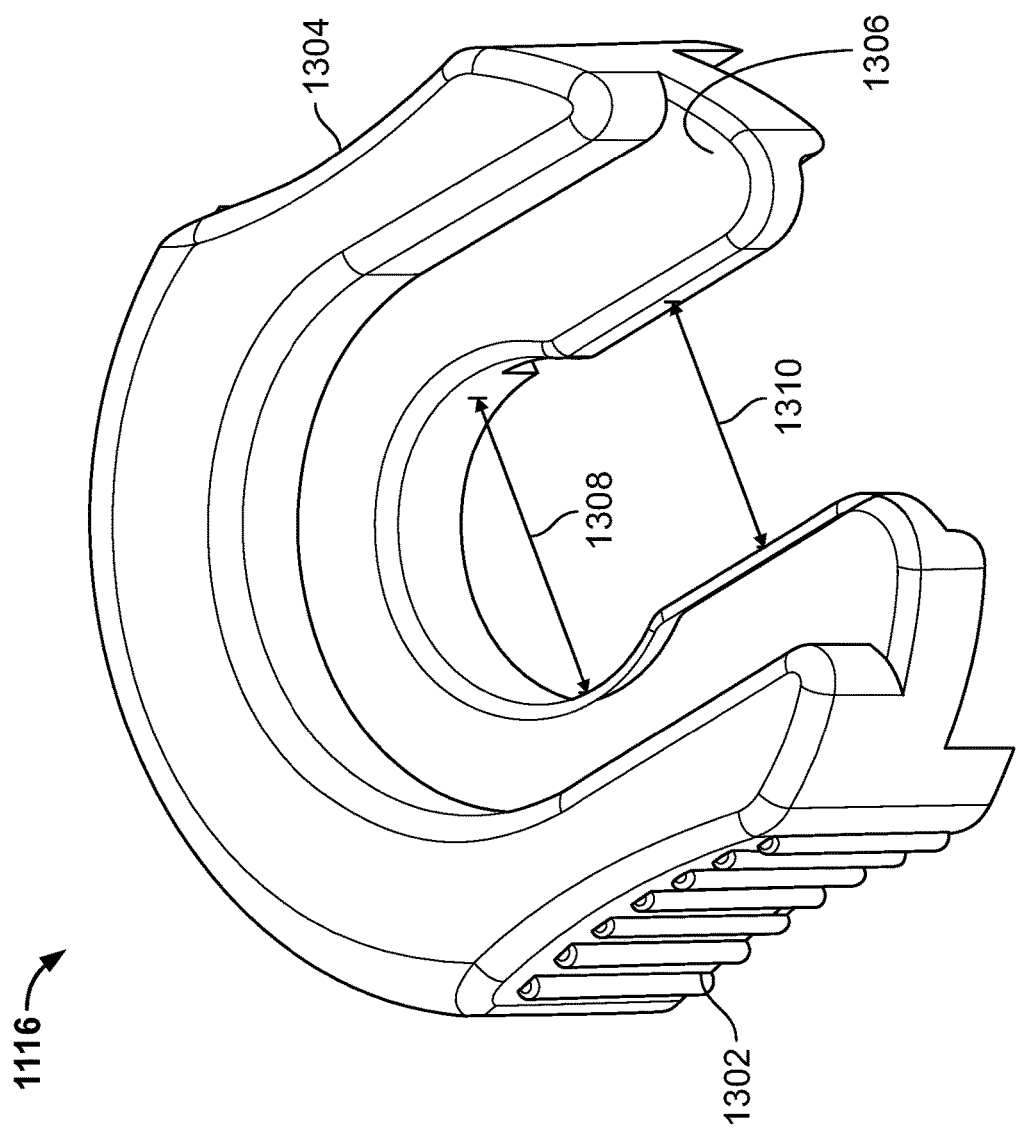
FIG. 25 shows an example ring of the injector assembly of FIG. 20.

The ring 1116 cannot be removed until the first dose is administered (i.e., the plunger portion 1114 has been pushed axially as shown). The plunger portion 1114 extends through the ring 1116. The ledge 1306 formed by the ring 1116 forms a first diameter 1308 sized to allow a barrel 1402 of the plunger portion 1114 to extend therethrough prior to administration of the first dose. See FIGS. 24-25. A second diameter 1310 of an open end of the ring 1116 narrows so that the ring 1116 cannot be removed because a diameter 1410 of the plunger portion 1114 is larger than the second diameter 1310 of the ledge 1302 of the ring 1116.

Once the plunger portion 1114 is moved axially to administer the first dose, a groove 1404 formed in the barrel 1402 of the plunger portion 1114 is positioned to correspond axially with the ring 1116. As this point, the groove 1404 has a diameter 1412 smaller than that of the second diameter 1310 of the ledge 1306. This allows the ring 1116 to clear the plunger portion 1114 and be removed.

This assures that the ring 1116 is not removed prior to administration of the first dose. Such a configuration is desirable, because the ring 1116 allows only a single dose to be provided for the first dose. In other words, if the ring 1116 could be removed prior to administration of the first dose, it is possible for both doses to be improperly administered at the same time, which is undesirable.

Figure 23:
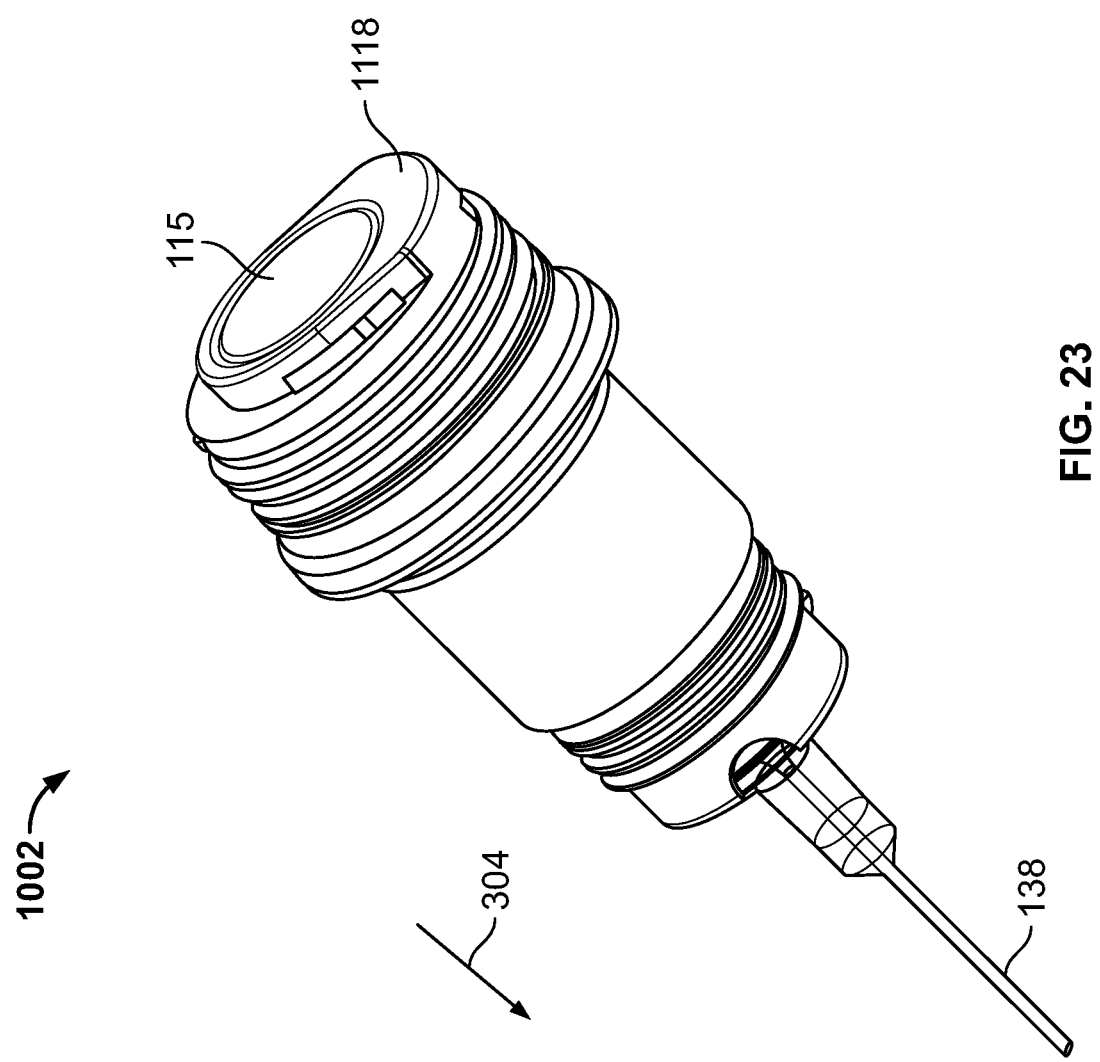
FIG. 23 shows another view of the injector assembly of FIG. 20 after administration of the second dose of medication.

Once the ring 1116 is removed, the plunger portion 1114 can be pushed further in the axial direction 304 into the barrel portion 112 to force the second dose of the medication through the needle shaft 138 and into the patient. The second dose is complete when the head 115 of the plunger portion 1114 bottoms out against the cap 1118. At that point, a proper amount of the medication has been forced out of the barrel portion 112 for the second dose, as shown in FIG. 23.

There can be various advantages to the configurations described herein. For example, the systems described herein can allow for multiple doses of a medication to be administered using a single device. This obviates the need for a patient to carry multiple devices for situations when a first dose is not sufficiently effective. Further, the systems described herein are easy to carry and use for administration of the medicine.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A device for administrating a liquid medication, the device comprising:
   a syringe assembly comprising:
      a barrel portion containing liquid medication;
      a plunger portion sealingly engaged with the barrel portion to form a chamber for expelling the liquid medication from the barrel portion; and
      a needle; and
   a ring positioned about the plunger portion of the syringe assembly, wherein the ring limits movement of the plunger portion in an axial direction as the plunger portion is moved in the axial direction to administer a first dose of the liquid medication;
   wherein the ring cannot be removed prior to an administration of the first dose;
   wherein, upon the administration of the first dose, the ring is removable to allow the plunger portion to be moved further in the axial direction for administration of a second dose;
   wherein the ring forms a central opening having a central opening diameter and a side opening having a width smaller than the central opening diameter of the central opening;
   wherein, prior to the administration of the first dose, the plunger portion has a plunger portion diameter smaller than the central opening diameter to allow the plunger portion to extend through the central opening of the ring, and the plunger portion diameter is larger than the width of the side opening so that the ring cannot be removed from the barrel portion;
   wherein the plunger portion includes a circumferential groove around the plunger portion located adjacent to a head coupled to the plunger portion, the circumferential groove having a groove diameter that is smaller than the width of the side opening of the ring;
   wherein, upon the administration of the first dose, the circumferential groove of the plunger portion is positioned at the ring so that the ring is removeable from the barrel portion by pulling the ring so that the plunger portion at the circumferential groove is moved through the side opening of the ring; and
   wherein, upon removal of the ring, the plunger portion is allowed to be moved further in the axial direction for the administration of the second dose.

\* \* \* \* \*